(12) United States Patent
Stancer et al.

(10) Patent No.: US 8,428,744 B2
(45) Date of Patent: Apr. 23, 2013

(54) IMPLANTABLE MEDICAL DEVICE WITH INDUCTIVE ANTENNA FILTER

(75) Inventors: Christopher C. Stancer, Prescott, WI (US); Steven J. Fraasch, Maple Grove, MN (US); Anthony C. French, Andover, MN (US); Kent E. Samuelson, Parker, CO (US); Farren L. Forcier, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 647 days.

(21) Appl. No.: 12/507,976

(22) Filed: Jul. 23, 2009

(65) Prior Publication Data

US 2011/0022123 A1 Jan. 27, 2011

(51) Int. Cl.
*A61N 1/00* (2006.01)
(52) U.S. Cl.
USPC ................................. 607/60; 607/30; 607/32
(58) Field of Classification Search ............... 607/30, 607/32, 61
See application file for complete search history.

(56) References Cited

U.S. PATENT DOCUMENTS

| | | | |
|---|---|---|---|
| 5,217,010 A | 6/1993 | Tsitlik et al. | |
| 5,697,958 A | 12/1997 | Paul et al. | |
| 6,298,271 B1 | 10/2001 | Weijand | |
| 6,453,200 B1 | 9/2002 | Koslar | |
| 6,456,256 B1 * | 9/2002 | Amundson et al. | 343/873 |
| 6,463,329 B1 | 10/2002 | Goedeke | |
| 6,535,766 B1 | 3/2003 | Thompson et al. | |
| 6,574,510 B2 * | 6/2003 | Von Arx et al. | 607/60 |
| 6,868,288 B2 | 3/2005 | Thompson | |
| 6,987,660 B2 | 1/2006 | Stevenson et al. | |
| 7,015,393 B2 | 3/2006 | Weiner et al. | |
| 7,072,718 B2 | 7/2006 | Von Arx et al. | |
| 7,199,995 B2 | 4/2007 | Stevenson | |
| 7,225,029 B2 | 5/2007 | Shankar et al. | |
| 2002/0026224 A1 * | 2/2002 | Thompson et al. | 607/60 |
| 2004/0199069 A1 | 10/2004 | Connelly et al. | |

(Continued)

FOREIGN PATENT DOCUMENTS

| | | |
|---|---|---|
| WO | 2007013917 | 2/2007 |
| WO | 2007102893 | 9/2007 |
| WO | 2008077037 | 6/2008 |

OTHER PUBLICATIONS (PCT/US2010/031167) PCT Notification of Transmittal of the International Search Report and the Written Opinion of the International Searching Authority, Mailed Jul. 19, 2010, 8 pages.

*Primary Examiner* — Nicole F Lavert
(74) *Attorney, Agent, or Firm* — Stephen W. Bauer; Michael J. Ostrom

(57) ABSTRACT

This disclosure describes techniques for reducing, and possibly eliminating, adverse effects caused by signals induced on an inductive antenna of an implanted medical device by varying magnetic fields from a source of interference, such as the gradient magnetic fields applied during an MRI procedure. For example, the implantable medical device includes an inductive antenna that receives signals via inductive coupling, a filter circuit that attenuates signals induced on the inductive antenna by varying magnetic fields generated from a source of interference and substantially passes signals induced on the inductive antenna by varying magnetic fields generated by an expected source and a telemetry module that processes the signals from the filter circuit.

22 Claims, 6 Drawing Sheets

U.S. PATENT DOCUMENTS

| | | |
|---|---|---|
| 2007/0043399 A1 | 2/2007 | Stevenson et al. |
| 2007/0067004 A1 | 3/2007 | Boveja et al. |
| 2007/0123949 A1 | 5/2007 | Dabney et al. |
| 2007/0179554 A1 | 8/2007 | Iyer et al. |
| 2008/0039709 A1 | 2/2008 | Karmarkar |
| 2008/0051854 A1 | 2/2008 | Bulkes et al. |
| 2008/0071313 A1 | 3/2008 | Stevenson et al. |
| 2008/0195180 A1 | 8/2008 | Stevenson et al. |
| 2008/0228270 A1 | 9/2008 | Dahlberg |
| 2009/0111390 A1 | 4/2009 | Sutton et al. |

* cited by examiner

IMPLANTABLE MEDICAL DEVICE WITH INDUCTIVE ANTENNA FILTER

TECHNICAL FIELD

The disclosure relates generally to implantable medical devices and, in particular, to filtering signals induced on an inductive antenna of the implantable medical device.

BACKGROUND

A wide variety of implantable medical devices (IMDs) that deliver a therapy to or monitor a physiologic or biological condition of a patient, or both, have been clinically implanted or proposed for clinical implantation in patients. The IMD may deliver therapy to or monitor a physiological or biological condition with respect to a variety of organs, nerves, muscles or tissues of the patients, such as the heart, brain, stomach, spinal cord, pelvic floor, or the like. The therapy provided by the IMD may include electrical stimulation therapy, drug delivery therapy or the like.

A patient in which the IMD is implanted is generally recommended to avoid sources that may interfere with operation of the IMD. These sources of interference may be medical sources or non-medical sources. One example medical source of interference is magnetic resonance imaging (MRI), which is an imaging technique to visualize the internal structure and function of the body. MRI systems typically use a strong static magnetic field, a varying gradient magnetic field, and radiofrequency (RF) pulses used to produce an image. Subjecting the IMD to such an environment may cause inappropriate operation of or damage to the IMD.

SUMMARY

This disclosure relates to techniques for reducing, and possibly eliminating, adverse effects caused by signals induced on an inductive antenna of an IMD by varying magnetic fields from a source of interference, such as the gradient magnetic fields applied during an MRI procedure. The signals induced on the inductive antenna by the varying magnetic fields from the source of interference may damage telemetry circuitry or other circuitry of the IMD and/or cause heating of the IMD that may damage tissue adjacent to the IMD. Although the techniques of this disclosure are described primarily with reference to varying magnetic fields generated during an MRI procedure, the techniques may be used to reduce adverse effects caused by varying magnetic fields from other sources of interference.

In one example, this disclosure is directed to an implantable medical device comprising an inductive antenna that receives signals via inductive coupling, a filter circuit that attenuates signals induced on the inductive antenna by varying magnetic fields generated from a source of interference and substantially passes signals induced on the inductive antenna by varying magnetic fields generated by an expected source, and a telemetry module that processes the signals from the filter circuit.

In another example, this disclosure is directed to an implantable medical device comprising means for receiving signals via inductive coupling, means for filtering the received signals to attenuate signals induced on the inductive antenna by varying magnetic fields generated from a source of interference and substantially pass signals induced on the inductive antenna by varying magnetic fields generated by an expected source, and means for processing the signals from the filter circuit.

In another example, this disclosure is directed to a method comprising receiving a signal via inductive coupling, filtering the received signal to attenuates signals induced on the inductive antenna by varying magnetic fields generated from a source of interference and substantially passes signals induced on the inductive antenna by varying magnetic fields generated by an expected source, and processing the signals output from the filter circuit.

This summary is intended to provide an overview of the subject matter described in this disclosure. It is not intended to provide an exclusive or exhaustive explanation of the invention as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

This disclosure describes techniques for reducing, and possibly eliminating, adverse effects caused by signals induced on an inductive antenna of an implanted medical device by varying magnetic fields from a source of interference, such as the gradient magnetic fields applied during an MRI procedure. For example, the implantable medical device includes an inductive antenna that receives signals via inductive coupling, a filter circuit that attenuates signals induced on the inductive antenna by varying magnetic fields generated from a source of interference and substantially passes signals induced on the inductive antenna by varying magnetic fields generated by an expected source and a telemetry module that processes the signals from the filter circuit.

Filtering the signals on the inductive antenna to attenuate signals induced on the inductive antenna by the source of interference may prevent damage to telemetry circuitry or other circuitry of the IMD. Additionally, filtering the signals on the inductive antenna to attenuate the signals induced on the inductive antenna by the source of interference may also reduce heating of the IMD, thus reducing the likelihood of damage to tissue adjacent to the IMD. Although the techniques of this disclosure are described primarily with reference to varying magnetic fields generated during an MRI procedure, the techniques may be used to reduce adverse effects caused by varying magnetic fields from other sources of interference, such as large AC and RF power transformers, high power broadcast sources (e.g., AM, FM and TV stations), high current welding equipment, powerful electric motors, inductive ranges and electronic article surveillance (EAS) gates (particularly magneto-harmonic variety) or other source that provides large varying magnetic fields.

Figure 1:
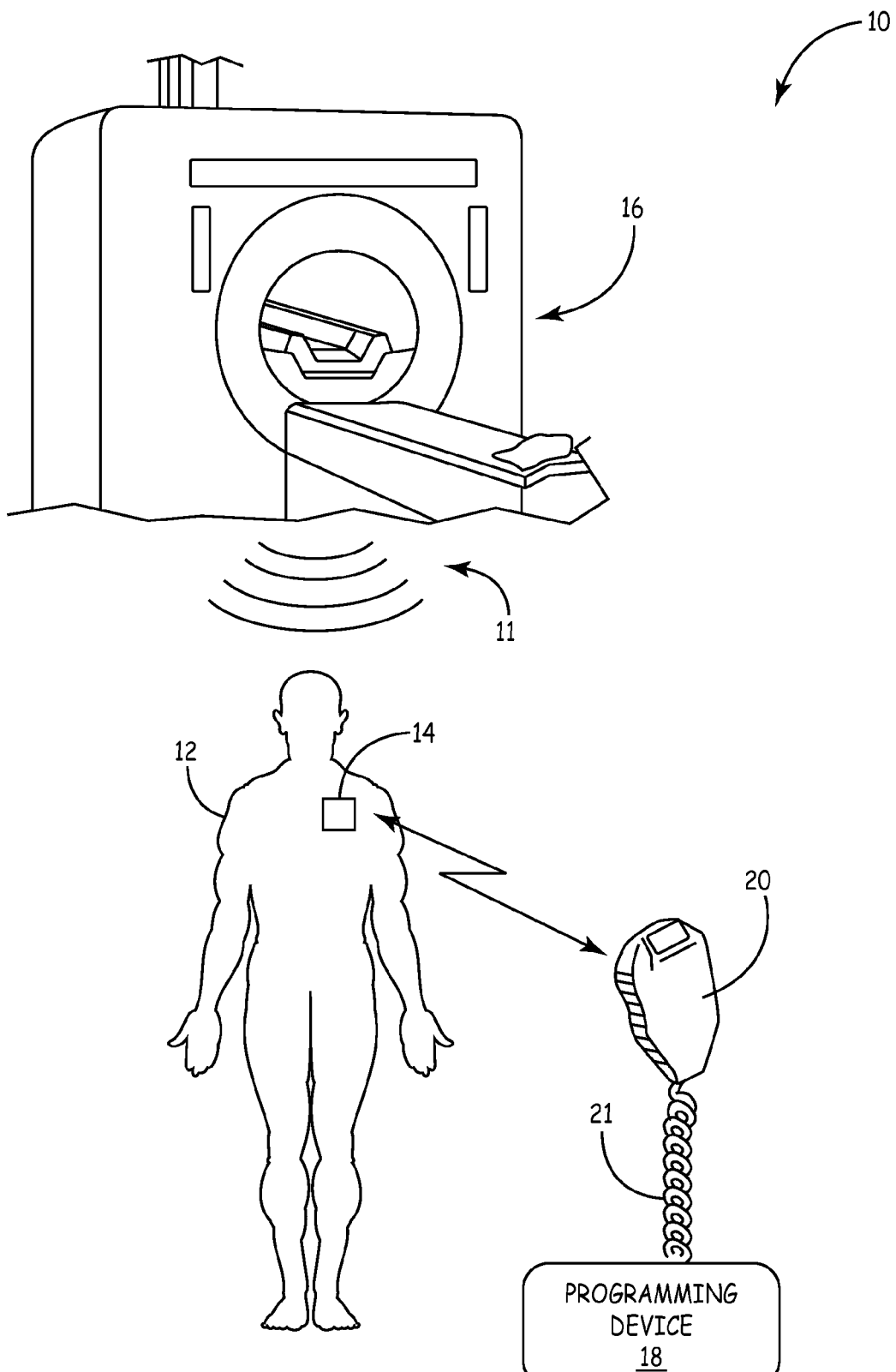
FIG. 1 is a conceptual diagram illustrating an environment in which an implantable medical device (IMD) is exposed to a source of interference that generates disruptive energy fields, including varying magnetic fields.

FIG. 1 is a conceptual diagram illustrating an environment 10 in which an implantable medical device (IMD) 14 is exposed to a source of interference that generates disruptive energy fields, including varying magnetic fields. IMD 14 is implanted within patient 12 to provide therapy to or to monitor a physiological or biological condition of patient 12. Patient 12 ordinarily, but not necessarily, will be a human.

IMD 14 may be any of a variety of therapy devices. For example, IMD 14 may be a device that provides electrical stimulation therapy via one or more implantable leads that include one or more electrodes (not shown). In some instances, IMD 14 may be a device that provides electrical stimulation therapy in the form of cardiac rhythm management therapy to a heart of patient 12 via leads implanted within one or more atria and/or ventricles of the heart. The cardiac rhythm management therapy delivered by IMD 14 may include pacing, cardioversion, defibrillation and/or cardiac resynchronization therapy (CRT). In other instances, IMD 14 may be a device that provides electrical stimulation to a tissue site of patient 12 proximate any muscle, organ or nerve, such as a tissue proximate a vagus nerve, spinal cord, brain, stomach, pelvic floor or the like.

In addition to providing electrical stimulation therapy, IMD 14 may sense one or more physiological or biological parameters of patient 12. When one or more leads are implanted within the heart of patient 12, for example, electrodes of the leads may sense electrical signals attendant to the depolarization and repolarization of the heart to monitor a rhythm of the heart or detect particular heart conditions, e.g., tachycardia, bradycardia, fibrillation or the like. The sensed electrical signals may, for example, comprise an electrogram (EGM) of the heart. IMD 14 may sense a variety of other physiologic parameters or other parameters related to a condition of patient 12, including, for example, neurologic parameters, intracardiac or intravascular pressure, activity, posture, pH of blood or other bodily fluids or the like.

In other instances, IMD 14 may be a device that delivers a drug or therapeutic agent to patient 12 via a catheter. IMD 14 may deliver, e.g., using a pump, the drug or therapeutic agent to a specific location of patient 12. IMD 14 may deliver the drug or therapeutic agent at a constant or variable flow rate. Drug pumps, infusion pump or drug delivery devices may be used to treat symptoms of a number of different conditions. For example, IMD 14 may deliver morphine or ziconotide to reduce or eliminate pain, baclofen to reduce or eliminate spasticity, chemotherapy to treat cancer, or any other drug or therapeutic agent (including saline, vitamins, etc.) to treat any other condition and/or symptom of a condition.

A user, such as a physician, technician, or other clinician, may interact with a programming device 18 to communicate with IMD 14. The user may interact with programming device 18 to retrieve physiological or diagnostic information from IMD 14. For example, the user may use programming device 18 to retrieve information from IMD 14 regarding the rhythm of the heart of patient 12, trends therein over time, or cardiac arrhythmia episodes. As another example, the user may use programming device 18 to retrieve information from IMD 14 regarding other sensed physiological parameters of patient 12, such as EGM, intracardiac or intravascular pressure, activity, posture, respiration or thoracic impedance. As a further example, the user may use programming device 18 to retrieve information from IMD 14 regarding the performance or integrity of IMD 14 or other components of therapy system 20, such as leads or a power source of IMD 14.

The user may also interact with programming device 18 to program IMD 14, e.g., select values for operational parameters of IMD 14. For electrical stimulation therapies, for example, the user may interact with programming device 18 to program a therapy progression, select an electrode or combination to use for delivering electrical stimulation (pulses or shocks), select parameters for the electrical pulse or shock (e.g., pulse amplitude, pulse width, or pulse rate), select electrodes or sensors for use in detecting a physiological parameter of patient 12, or the like. By programming these parameters, the physician or other user can attempt to generate an efficacious therapy for patient 12 that is delivered via the selected electrodes.

Programming device 18 may be a dedicated hardware device with dedicated software for programming of IMD 14. Alternatively, programming device 18 may be an off-the-shelf computing device running an application that enables programming device 18 to program IMD 14. Programming device 18 may include a user interface that receives input from the user and/or displays data to the user.

Programming device 18 may be coupled to a telemetry head 20 that may be placed proximate to the patient's body near the implant site of IMD 14 in order to improve the quality and/or security of communication between IMD 14 and programming device 18. In the example illustrated in FIG. 1, telemetry head 20 may be connected to programming device 18 via a cable 21. Other connecting mechanisms may be used to couple telemetry head 20 to programming device 18, including wireless connectivity such as Bluetooth. In other instances, programming device 18 may be a handheld computing device that may be placed proximate to the patient's body near the implant site of IMD 14. In this case, programming device 18 may not be coupled to a telemetry head since the device itself may be placed in close proximity to patient 12.

Programming device 18 may communicate with IMD 14 via wireless communication using any techniques known in the art. For example, telemetry head 20 may include an inductive antenna that transmits signals to and receives signals from an inductive antenna of IMD 14 via inductive coupling. Inductive coupling refers to the transfer of energy from one antenna to the other antenna by means of mutual inductance between the two antennas. In particular, energy is transferred between the inductive antennas by a changing magnetic flux through the antennas. Inductive coupling may require that the antennas are physically located in close proximity with one another. In the case of IMD 14, for example, the inductive antenna of IMD 14 and the inductive antenna of telemetry head 20 may need to be located within one foot of one another and more preferable within several inches of one another.

IMD 14 may, in some instances, be capable of wireless communication at farther distances using RF telemetry in addition to the communication via inductive coupling. In such cases, IMD 14 may include a separate RF antenna for receiving RF communications at distances of greater than one foot. In fact, the IMD 14 may be capable of communicating with programming device 18 at distances up to or exceeding one meter. In the case of RF telemetry, the user may not need to place telemetry head 20 in close proximity to the site of implantation of IMD 14. Instead, the RF antenna of IMD 14 may transmit signals to and receive signals from an RF antenna located within or otherwise attached to programming device 18.

Environment 10 includes a source of interference that generates disruptive energy fields, including varying magnetic fields, to which IMD 14 is exposed. In the example illustrated in FIG. 1, the source of interference is an MRI scanner 16. MRI scanner 16 uses magnetic and radio frequency (RF) fields to produce images of internal body structures to diagnose injuries and/or disorders. In particular, MRI scanner 16 generates a static magnetic field, gradient magnetic fields and RF fields that are applied in a particular order to generate the image of the body structures of patient 12. The static magnetic field is a non-varying magnetic field that is typically always present around MRI scanner 16 whether or not a MRI scan is in progress. Gradient magnetic fields 11 are low-frequency, varying magnetic fields that are typically only present while the MRI scan is in progress. RF fields are pulsed RF fields that are also typically only present while the MRI scan is in progress. The order in which the fields are applied, the timing of the application of the various fields and the number of times the fields are applied may depend on the desired image to be obtained.

Some or all of the various types of fields produced by MRI scanner 16 may interfere with operation of IMD 14 or have other adverse effects. For example, gradient magnetic fields 11 produced by MRI scanner 16 may induce signals on the inductive antenna of IMD 14 via inductive coupling. The induced signals on the inductive antenna may cause damage to one or more components of IMD 14, such as telemetry circuitry of IMD 14. The induced signals on the inductive antenna may also result in an increase in heating of IMD 14, which may cause thermal damage to the tissue adjacent to IMD 14.

To reduce the undesirable effects of gradient magnetic fields 11, e.g., damage, incorrect operation and/or gradient heating, IMD 14 filters the signals of the inductive antenna to attenuate signals induced by gradient magnetic fields 11 associated with MRI scanner 16. Thus, IMD 14 substantially blocks the signals induced on the inductive antenna by gradient magnetic fields 11 associated with MRI scanner 16 while substantially passing signals induced on the inductive antenna by an expected source, such as signals from programming device 18 or a home monitoring device (not shown). For example, IMD 14 may include a high pass filter that substantially passes actual telemetry signals while substantially blocking signals induced by gradient magnetic fields 11 generated by MRI scanner 16. Other filtering mechanisms may also be used, such as band pass or band stop filters. Although the techniques of this disclosure are described with respect to gradient magnetic fields 11 generated by MRI scanner 16, the techniques may be used to attenuate signals induced by any varying magnetic fields from other sources of interference described above.

In addition to the undesirable effects caused by the signals induced on the inductive antenna by gradient magnetic fields 11, other undesirable effects may be caused by the gradient magnetic fields, the static magnetic field and/or the RF pulses of MRI scanner 11. As such, the filtering techniques to reduce the effects of the signals induced on the inductive antenna from gradient magnetic fields 11 may be used in conjunction with other techniques aimed at reducing interference due to the static magnetic field or the pulsed RF signals.

Figure 2:
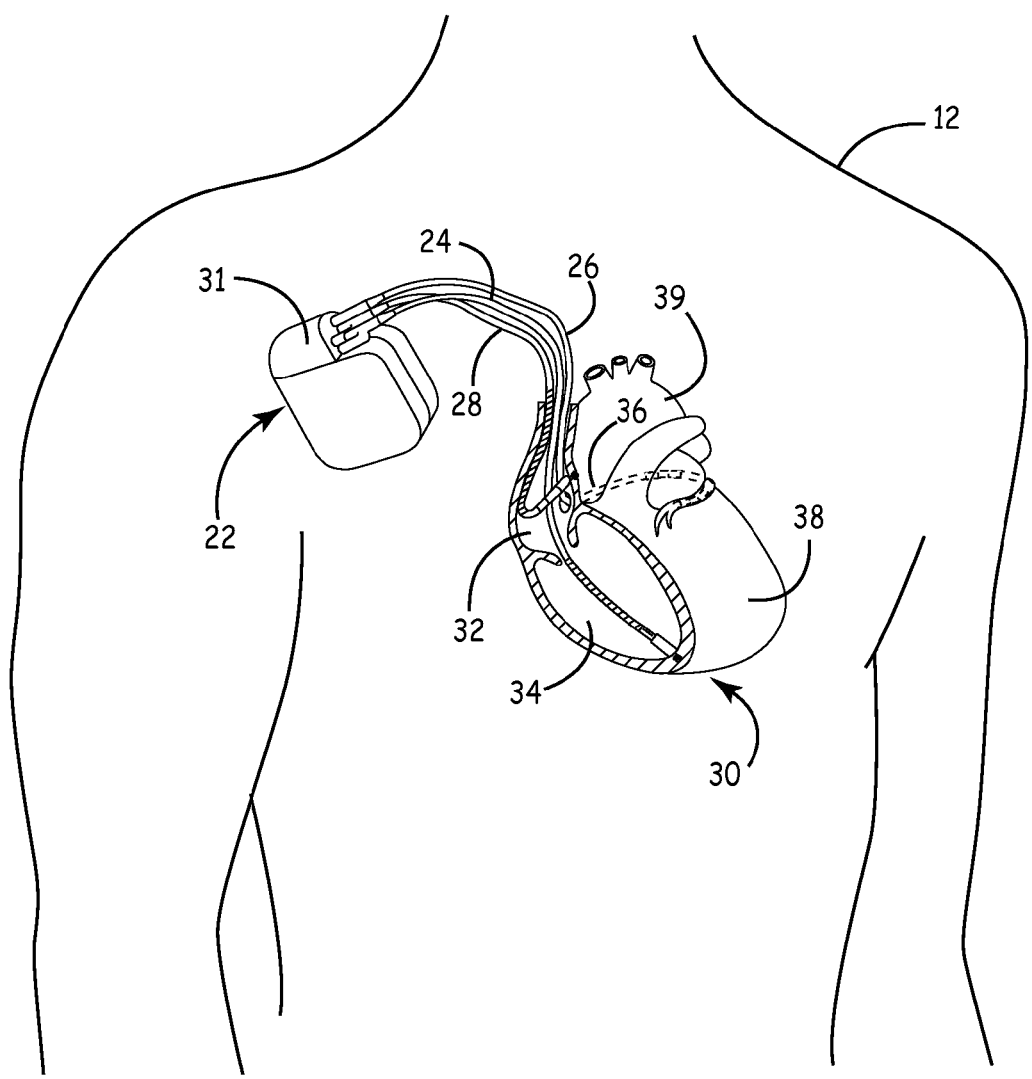
FIG. 2 is a conceptual diagram illustrating an example IMD that may be used to provide therapy to patient and/or monitor a physiological condition of a heart of a patient.

FIG. 2 is a conceptual diagram illustrating an example IMD 22 that may be used to provide therapy to patient 12 and/or monitor a physiological condition of patient 12. IMD 22 may correspond to IMD 14 of FIG. 1. In the example illustrated in FIG. 2, IMD 22 is an implantable cardiac device that provides electrical stimulation therapy to a heart 30 of patient 12. The electrical stimulation therapy to heart 30, sometimes referred to as cardiac rhythm management therapy, may include pacing, cardioversion, defibrillation and/or CRT. As such, IMD 22 may operate as an implantable pacemaker, cardioverter, and/or defibrillator or CRT device.

IMD 22 may deliver the electrical stimulation therapy to heart 30 via electrodes coupled to leads 24, 26 and/or 28 that are implanted within or adjacent to one or more atria or ventricles of heart 30. Leads 24, 26 and 28 may be coupled to circuitry within IMD 22 via connector block 31. In the example illustrated in FIG. 2, leads 24, 26 and 28 are coupled to IMD 22 and extend into heart 30 of patient 12. In the example shown in FIG. 2, right ventricular (RV) lead 24 extends through one or more veins, the superior vena cava, and right atrium 32, and into right ventricle 34 of heart 30. Left ventricular (LV) coronary sinus lead 26 extends through one or more veins, the vena cava, right atrium 32, and into the coronary sinus 36 to a region adjacent to the free wall of left ventricle 38 of heart 30. Right atrial (RA) lead 28 extends through one or more veins and the vena cava, and into the right atrium 32 of heart 30. In other examples, IMD 22 may deliver stimulation therapy to heart 30 by delivering stimulation to an extravascular tissue site in addition to or instead of delivering stimulation via electrodes of intravascular leads 24, 26 and 28.

In addition to delivering therapy to heart 30, electrodes of leads 24, 26 and 28 may sense electrical signals attendant to the depolarization and repolarization of heart 30 (e.g., cardiac signals). IMD 22 may analyze the sensed signals to monitor a rhythm of the heart or detect an arrhythmia of heart 30, e.g., tachycardia, bradycardia, fibrillation or the like. In some instances, IMD 22 provides pacing pulses to heart 30 based on the cardiac signals sensed within heart 30. IMD 22 may also provide defibrillation therapy and/or cardioversion therapy via electrodes located on at least one of the leads 24, 26 and 28. IMD 22 may detect arrhythmia of heart 30 based on the sensed cardiac signals and deliver defibrillation therapy to heart 30 in the form of electrical shocks. In some examples, IMD 22 may be programmed to deliver a progression of therapies, e.g., shocks with increasing energy levels, until the arrhythmia of heart 30 is stopped.

The example IMD 22 illustrated in FIG. 2 is merely one example of an implantable medical device that may utilize the techniques of this disclosure. In other examples, IMD 22 may include more or fewer leads extending from IMD 22. For example, IMD 22 may be coupled to two leads, e.g., one lead implanted within right atrium 32 and the other implanted within right ventricle 34. In another example, IMD 22 may be coupled to a single lead that is implanted within either an atrium or ventricle of heart 30. As a further example, the therapy system may include three transvenous leads located as illustrated in FIG. 2, and an additional lead located within or proximate to left atrium 38. As such, IMD 22 may be used for single chamber or multi-chamber cardiac rhythm management therapy. In addition to more or fewer leads, each of leads 24, 26 and 28 may include more or fewer electrodes.

The techniques of this disclosure are described in the context of cardiac rhythm management therapy for purposes of illustration. The techniques of this disclosure, however, may be used to operate an IMD that provides other types of electrical stimulation therapy. For example, the IMD may be a device that provides electrical stimulation to a tissue site of patient 12 proximate a muscle, organ or nerve, such as a tissue proximate a vagus nerve, spinal cord, brain, stomach, pelvic floor or the like. Moreover, the techniques may be used to operate an IMD that provides other types of therapy, such as drug delivery or infusion therapies. As such, description of these techniques in the context of cardiac rhythm management therapy should not be limiting of the techniques as broadly described in this disclosure.

Figure 3:
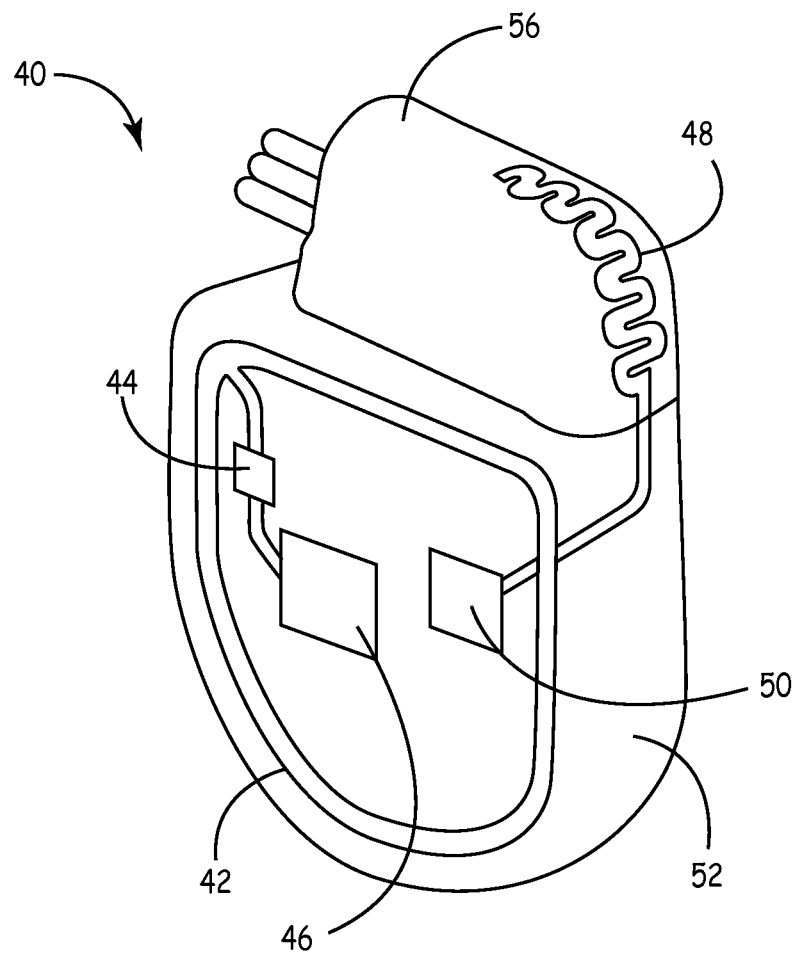
FIG. 3 is a schematic diagram of an example IMD that utilizes the techniques of this disclosure to reduce adverse effects caused by signals induced on an inductive antenna of IMD by a source of interference.

FIG. 3 is a schematic diagram of an example IMD 40 that utilizes the techniques of this disclosure to reduce adverse effects caused by signals induced on an inductive antenna 42 of IMD 40 by a source of interference. IMD 40 may correspond to IMD 14 of FIG. 1 or IMD 22 of FIG. 2. IMD 40 includes inductive antenna 42, a filter circuit 44 and an inductive telemetry module 46. IMD 40 may, in some instances, also include an RF antenna 48 and an RF module 50. In other instances, however, IMD 40 may include only inductive antenna 42 and not have a second antenna for communicating via RF.

In the example illustrated in FIG. 3, inductive antenna 42 comprises a loop antenna located within housing 52 of IMD 40. Inductive antenna 42 comprises one or more loops of conductive material and is located substantially adjacent to the interior perimeter of housing 52. In one particular example, inductive antenna 42 has a loop area of approximately one square inch and approximately 150 loops (or turns). However, the techniques of this disclosure are not limited to antennas of such a loop area, but instead may be applied to any size loop area including loop areas larger than one inch and smaller than one inch. Inductive loop antenna 42 of FIG. 3 is illustrated for purposes of example. Inductive loop antenna 42 may take on various shapes, such as rectangular, circular, triangular, square, oval or any other shape. Inductive loop antenna 42 may also have a larger or smaller loop area, and thus not be substantially adjacent to the interior perimeter of housing 52. For example, a multi-loop antenna may be located in a corner of the housing or elsewhere within the housing of the IMD, e.g., away from the perimeter of the housing.

As describe above, inductive antenna 42 transmits and receives signals via inductive coupling. In the context of receiving signals, for example, a changing magnetic flux through conductive material forming inductive antenna 42 induces a signal on inductive antenna 42. Some of the signals induced on inductive antenna 42 are expected and desirable, such as telemetry signals inductively coupled via telemetry head 20 connected to programming device 18 (FIG. 1). However, other signals induced on inductive antenna 42 are undesirable, such as signals induced on inductive antenna 42 by varying magnetic fields of a source of interference (e.g., gradient magnetic fields 11 of MRI scanner 16 of FIG. 1).

The undesirable signals may cause adverse effects, such as damage to one or more components of IMD 40 and/or undesirable heating of IMD 40. The signals induced on inductive antenna 42 may be larger, e.g., larger peak voltages or currents, for inductive antennas having larger loop areas and/or more loops (or turns). The signals induced on inductive antenna 42 by gradient magnetic fields 11 of MRI scanner 16 may be greater than approximately 25 milliamps and, in some instances, as large as 92 volts peak-to-peak ($V_{p-p}$) and induce currents as large as 188 milli-amps (mA). These large induced signals may damage components of IMD 40 and/or result in undesirable heating of IMD 40.

To reduce the adverse effects of the undesirable signals induced by gradient magnetic fields 11 of MRI scanner 16, IMD 40 includes filter circuit 44 to attenuate the undesirable signals. Filter circuit 44 may, in one example, include one or more capacitors and resistors arranged to form a high pass filter that substantially passes desired telemetry signals while substantially blocking undesired signals induced by gradient magnetic fields 11 generated by MRI scanner 16. In other examples, filter circuit 44 may include one or more capacitors, resistors and/or inductors arranged to form a band pass filter that substantially passes only the frequency associated with the desired telemetry signals or a band stop filter that substantially blocks the frequency associated with gradient magnetic fields 11 of MRI scanner 16. Although filter circuit 44 is illustrated as a separate component, filter circuit 44 and inductive telemetry module 46 may be incorporated into a single component, such as an integrated circuit (IC).

Inductive antenna 42 is also shielded from the RF pulses of MRI scanner 16 by housing 52. Housing 52 may be constructed of a conductive, non-magnetic material such as titanium. The RF pulses incident on housing 52 generate currents on housing 52, thereby substantially shielding inductive antenna 42 from RF pulses from MRI scanner 16.

RF antenna 48 is located at least partially outside of housing 52 of IMD 40. In the example illustrated in FIG. 3, RF antenna 48 is located in the connector block 56 of IMD 40. Connector block 56 is constructed of a non-conductive material such that RF signals are not shielded from RF antenna 48. In the example illustrated in FIG. 3, RF antenna 48 is formed of a conductive material that has a meander shape. RF antenna 48 may take on shapes other than meanders, such as a straight antenna, a folded antenna or the like.

RF antenna 48 transmits signals to and receives signals from programming device 18 using electric field propagation. Electric field propagation allows IMD 40 to be capable of wireless communication at farther distances than magnetic field or inductive coupling. In such cases, IMD 40 is capable of communicating using RF or inductive coupling based on the particular circumstances. RF telemetry module 50 processes the signals received via RF antenna 48 and provides signals for transmission to RF antenna 48. In some instances, the same telemetry module may be used for both inductive and RF signals.

Telemetry modules 46 and 50 include any suitable hardware, firmware, software or any combination thereof for communicating with another device, such as programming device 18. For example, telemetry module 38 may include appropriate modulation, demodulation, frequency conversion, and amplifier components for transmission and reception of data. Inductive telemetry module 46 and RF telemetry module 50 may include any one or more of a processor, a microprocessor, a controller, a digital signal processor (DSP), an application specific integrated circuit (ASIC), a field-programmable gate array (FPGA), or equivalent discrete or integrated logic circuitry. In some examples, inductive telemetry module 46 and RF telemetry module 50 may include multiple components, such as any combination of one or more microprocessors, one or more controllers, one or more DSPs, one or more ASICs, or one or more FPGAs, as well as other discrete or integrated logic circuitry. The functions attributed to control unit 58 herein may be embodied as software, firmware, hardware or any combination thereof.

Figure 4:
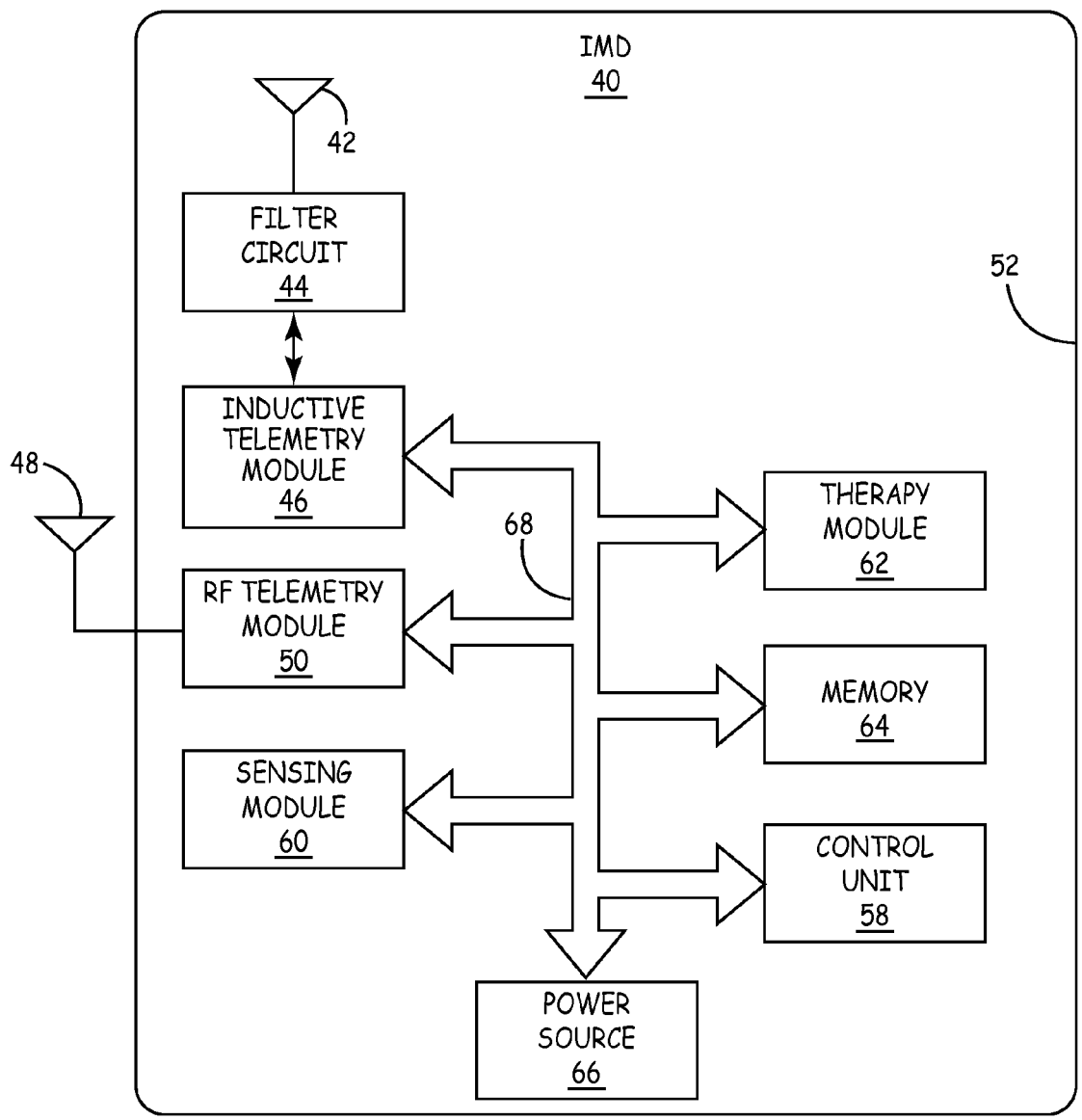
FIG. 4 is a block diagram illustrating example components of an example IMD.

FIG. 4 is a block diagram illustrating example components of IMD 40. IMD 40 includes an inductive antenna 42, filter circuit 44, inductive telemetry module 46, RF antenna 48, RF telemetry module 50, control unit 58, sensing module 60, therapy module 62, memory 64 and power source 66. Inductive telemetry module 46, RF telemetry module 50, control unit 58, sensing module 60, therapy module 62, memory 64 and power source 66 may be interconnected by a data bus 68, direct interconnects or other connections, or a combination thereof.

The various components of IMD 40 are coupled to power source 66, which may include a rechargeable or non-rechargeable battery. A non-rechargeable battery may be selected to last for several years, while a rechargeable battery may be charged from an external charging device on a daily or weekly basis. In either case, and especially in the case of the non-rechargeable battery, the amount of power of the battery is limited.

IMD 40 may sense one or more physiological signals or conditions of patient 12. In some instances, IMD 40 may not provide therapy to patient 12, but only provides monitoring of patient 12 as in the case of an implantable loop recorder. In such cases, IMD 40 may not include therapy module 62. Sensing module 60 is configured to monitor one or more physiological signals using one or more sensors connected to sensing module 60. In one example, sensing module 60 is configured to monitor signals sensed by one or more of electrodes on leads extending from IMD 40. In another example, sensing module 60 may be configured to monitor signals sensed by a sensor within or on IMD 40. In a further example, sensing module 60 may be configured to receive signals sensed by one or more wireless or lead-less sensors and transmitted wirelessly to IMD 40. The one or more sensors may sense physiological signals such as heart activity (e.g., electrocardiogram (ECG) signals), muscle activity (e.g., electromyography (EMG) signals), brain electrical activity (e.g., electroencephalography (EEG) signals), heart rate, intravascular pressure, blood pressure, blood flow, acceleration, displacement, motion, respiration, or blood/tissue chemistry such as oxygen saturation, carbon dioxide, pH, protein levels, enzyme levels or other biological, physiological or other type of parameter.

Sensing module 60 may store the sensed signals in memory 64. In some instances, sensing module 60 may store the sensed signals in raw form. In other instances, sensing module 60 may process the sensed signals and store the processed signals in memory 64. For example, sensing module 60 may amplify and filter the sensed signal and store the filtered signal in memory 64. The signals stored by sensing module 60 may, in some cases, be retrieved and further processed by control unit 58.

IMD 40 may also provide therapy, such as electrical stimulation therapy or drug delivery therapy, to patient 12 in accordance with parameters of one or more selected therapy programs. In particular, control unit 58 controls therapy module 62 to deliver therapy to patient 12 according to one or more therapy programs, which may be received from programming device 18 and stored in memory 64. In the case of electrical stimulation therapy, therapy module 62 may include a stimulation generator that generates and delivers electrical stimulation therapy, e.g., in the form of pulses or shocks. Control unit 58 may control the stimulation generator to deliver electrical stimulation pulses with amplitudes, pulse widths, frequency, and/or electrode polarities specified by the one or more therapy programs. In the case of drug delivery therapy, therapy module 62 may include a pump that delivers a drug or therapeutic agent to patient 12. Control unit 58 may control the pump to deliver the drug or therapeutic agent with the dosage and frequency (or rate) specified by the one or more therapy programs.

Control unit 58 may include any one or more of a processor, a microprocessor, a controller, a DSP, an ASIC, a FPGA, or equivalent discrete or integrated logic circuitry. In some examples, control unit 58 may include multiple components, such as any combination of one or more microprocessors, one or more controllers, one or more DSPs, one or more ASICs, or one or more FPGAs, as well as other discrete or integrated logic circuitry. The functions attributed to control unit 58 herein may be embodied as software, firmware, hardware or any combination thereof.

Memory 64 includes computer-readable instructions that, when executed by control unit 58, cause IMD 40 and control unit 58 to perform various functions attributed to IMD 40 and control unit 58 herein. Memory 64 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, magnetoresistive random access memory (MRAM), or any other digital media.

Control unit 58 controls inductive telemetry module 46 and/or RF telemetry module 50 to transmit communications to and/or receive communications from another medical device, such as programming device 18. Control unit 58 may provide the data to be transmitted to programming device 18 and the control signals for telemetry circuitry within telemetry modules 46 or 50, e.g., via data bus 68. Telemetry module 46 or 50 transmits the data to programming device 18 in accordance with the control signals from control unit 58. Telemetry module 46 or 50 may provide data received from programming device 18 to control unit 58. Control unit 58 may analyze the received data, store the received data within memory 64 and configure components of IMD 40 in accordance with the received data.

As described above, inductive telemetry module 46 transmits signals from and receives signals on inductive antenna 42 via inductive coupling. In some instances, inductive telemetry antenna 42 may be a loop antenna formed from one or more loops of conductive material. The loop area and number of loops depends on the particular application of inductive antenna 42. Inductive telemetry antenna 42 may comprise other types of antennas such as a helical antenna, spiral antenna, loop antennas with non-air cores, e.g., ferrite cores, or other antenna that communicates via inductive coupling.

Some of the signals induced on inductive antenna 42 are expected and desirable, such as telemetry signals inductively coupled via telemetry head 20 connected to programming device 18 (FIG. 1). However, other signals induced on inductive antenna 42 are undesirable, such as signals induced on inductive antenna 42 by varying magnetic fields of a source of interference (e.g., gradient magnetic fields 11 of MRI scanner 16 of FIG. 1). The signals induced on inductive antenna 42 are typically dependent on the loop area and the number of loops of inductive antenna 42. For example, larger signals (e.g., currents) are induced on inductive antennas with larger loop areas or more loops. Currents larger than approximately 25 milliamps and as large as approximately 200 milliamps may be induced on inductive antenna 42 by gradient magnetic fields 11 of MRI scanner 16. The undesirable signals may cause adverse effects, such as damage to one or more components of IMD 40 and/or undesirable heating of IMD 40, when the undesirable signals induced by gradient magnetic fields 11 become large enough.

To reduce the adverse effects of the undesirable signals induced by gradient magnetic fields 11 of MRI scanner 16, IMD 40 includes filter circuit 44 to attenuate the undesirable signals. Filter circuit 44 may, in one example, include one or more capacitors and resistors arranged to form a high pass filter that substantially passes desired telemetry signals while substantially blocking undesired signals induced by gradient magnetic fields 11 generated by MRI scanner 16. In other examples, filter circuit 44 may include one or more capacitors, resistors and/or inductors arranged to form a band pass filter that substantially passes only the frequency associated with the desired telemetry signals or a band stop filter that substantially blocks the frequency associated with gradient magnetic fields 11 of MRI scanner 16. Although filter circuit 44 is illustrated as a separate component, filter circuit 44 and inductive telemetry module 46 may be incorporated into a single component, such as an integrated circuit (IC).

Inductive antenna 42, which is located substantially within housing 52 of IMD 40, is also shielded from the RF pulses of MRI scanner 16 by housing 52. Housing 52 may be constructed of a conductive, non-magnetic material such as titanium. The RF pulses incident on housing 52 generate currents on housing 52, thereby substantially shielding inductive antenna 42 from RF pulses from MRI scanner 16.

RF antenna 48 is located at least partially outside of housing 52 of IMD 40, such as within a connector block 56 (FIG. 3) of IMD 40. RF antenna 48 transmits signals to and receives signals from programming device 18 using electric field propagation. Electric field propagation allows IMD 40 to be capable of wireless communication at farther distances than magnetic field or inductive coupling. In such cases, IMD 40 is capable of communicating using RF or inductive coupling based on the particular circumstances.

Figure 5:
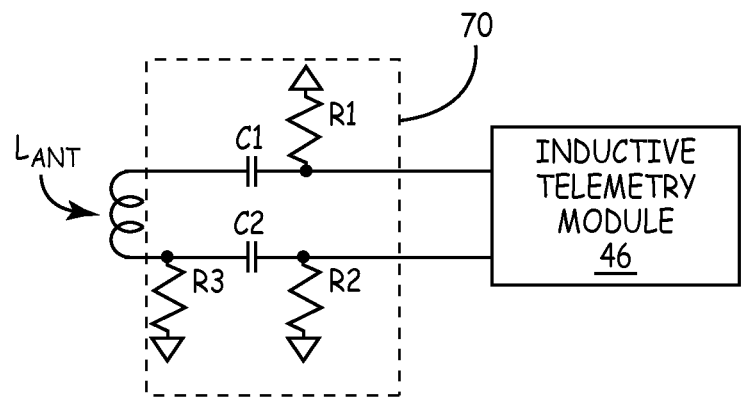
FIGS. 5-7 are circuit diagram illustrating example filter circuits that attenuate signals induced on the inductive antenna by varying magnetic fields generated from a source of interference and substantially pass signals induced on the inductive antenna by varying magnetic fields generated by an expected source.
Figure 6:
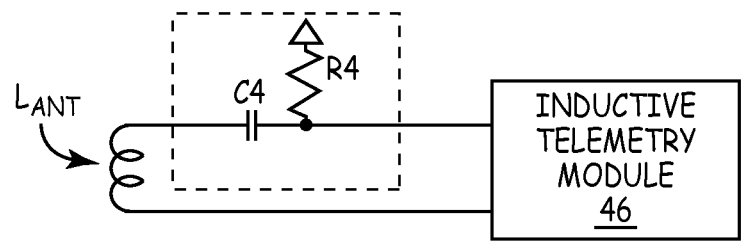
Figure 7:
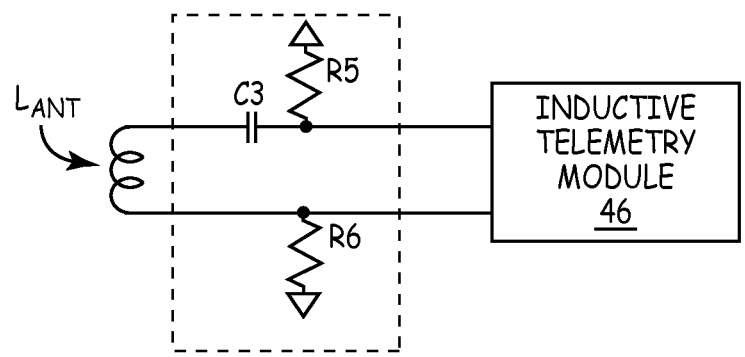

FIGS. 5-7 are circuit diagram illustrating example filter circuits that attenuate signals induced on the inductive antenna by varying magnetic fields generated from a source of interference and substantially pass signals induced on the inductive antenna by varying magnetic fields generated by an expected source. The various example filter circuits may correspond with filter circuit 44 of FIGS. 3 and 4.

FIG. 5 is circuit diagram illustrating an example high pass filter circuit 70 connected between an inductive antenna, represented by inductor $L_{ant}$, and inductive telemetry module 46. High pass filter circuit 70 includes resistors $R_1$, $R_2$, and $R_2$ and capacitors $C_1$ and $C_2$. The inductive antenna has two terminals, the two terminals of inductor $L_{ant}$ in FIG. 5, that feed two terminals of inductive telemetry module 46. High pass filter circuit 70 is arranged between the inductive antenna and the inductive telemetry module 46. In particular, high pass filter circuit 70 include a capacitor $C_1$ connected in series between a first terminal of $L_{ant}$ and a first terminal of inductive telemetry module 46. High pass filter circuit also includes a resistor $R_1$ that has a first terminal connected to a terminal of capacitor $C_1$ and the first terminal of telemetry module 46 and a second terminal connected to a reference, such as ground.

High pass filter circuit 70 also includes a capacitor $C_2$ connected in series between a second terminal of $L_{ant}$ and a second terminal of inductive telemetry module 46. High pass filter circuit 70 also includes a resistor $R_2$ that has a first terminal connected to a terminal of capacitor $C_2$ and the second terminal of telemetry module 46 and a second terminal connected to a reference, such as ground. High pass filter circuit 70 also includes another resistor $R_3$ that has a first terminal connected to the other terminal of capacitor $C_2$ and the second terminal of the inductive antenna and a second terminal connected to a reference, such as ground. In this manner, resistor $R_3$ provides a static drain path for the capacitors to the implantable device ground to remove any residual voltage on the capacitors, e.g., due to mismatch in capacitors $C_1$ and $C_2$. The resistive value of $R_3$ may be substantially larger than the resistive value of $R_1$ and $R_2$.

High pass filter circuit 70 operates as a fully differential high pass filter to substantially block signals induced on the inductive antenna by varying magnetic fields generated from a source of interference and substantially pass signals induced on the inductive antenna by varying magnetic fields generated by an expected source. In this particular example, high pass filter circuit 70 substantially blocks signals from gradient magnetic fields 11 of MRI scanner 16, which occur at frequencies typically less than 10 kHz, and pass telemetry signals from programming device 18, which occur around approximately 175 kHz. As such, the components of filter circuit 70 are selected to substantially block the signals of the interfering varying magnetic fields. In one example, $C_1$ and $C_2$ may take on values approximately equal to 18 nF, resistors $R_1$ and $R_2$ may have values of approximately 10 kΩ, and $R_3$ may be approximately 1 MΩ. Other capacitive and/or resistive values may be used to form high pass filter circuit 70. Moreover more or fewer capacitors and resistors may be used.

FIG. 6 is circuit diagram illustrating another example high pass filter circuit 80 connected between an inductive antenna, represented by inductor $L_{ant}$, and inductive telemetry module 46. High pass filter circuit 80 includes resistor $R_4$ and capacitor $C_4$. The inductive antenna has two terminals, the two terminals of inductor $L_{ant}$ in FIG. 6, that feed two terminals of inductive telemetry module 46. High pass filter circuit 80 is arranged between the inductive antenna and the inductive telemetry module 46. In particular, capacitor $C_4$ of high pass filter circuit 80 is connected in series between a first terminal of $L_{ant}$ and a first terminal of inductive telemetry module 46. Resistor $R_4$ of high pass filter circuit 80 has a first terminal connected to a terminal of capacitor $C_4$ and the first terminal of telemetry module 46 and a second terminal connected to a reference, such as ground.

Unlike high pass filter circuit 70 of FIG. 5, high pass filter circuit 80 does not include any components coupled between the second terminal of $L_{ant}$ and the second terminal of inductive telemetry module 46. As such, high pass filter circuit 80 operates as a single ended high pass filter circuit. The resistive and capacitive values of $R_4$ and $C_4$ are selected such that high pass filter circuit 80 operates to substantially block signals induced on the inductive antenna by varying magnetic fields generated from a source of interference and substantially pass signals induced on the inductive antenna by varying magnetic fields generated by an expected source.

In this particular example, high pass filter circuit 80 substantially blocks signals from gradient magnetic fields 11 of MRI scanner 16, which occur at frequencies less than 10 kHz, and pass telemetry signals from programming device 18, which occur around approximately 175 kHz. As such, the components of filter circuit 80 are selected to substantially block the signals of the interfering varying magnetic fields. In one example, $R_4$ and $C_4$ may take on values approximately equal to 10 kΩ and 18 nF, respectively. However, other capacitive and/or resistive values may be used to form high pass filter circuit 80. Moreover more or fewer capacitors and resistors may be used.

FIG. 7 is circuit diagram illustrating another example high pass filter circuit 90 connected between an inductive antenna, represented by inductor $L_{ant}$, and inductive telemetry module 46. High pass filter circuit 90 includes resistors $R_5$ and $R_6$ and capacitor $C_5$. The inductive antenna has two terminals, the two terminals of inductor $L_{ant}$ in FIG. 6, that feed two terminals of inductive telemetry module 46. High pass filter circuit 90 is arranged between the inductive antenna and the inductive telemetry module 46. In particular, capacitor $C_5$ of high pass filter circuit 90 is connected in series between a first terminal of $L_{ant}$ and a first terminal of inductive telemetry module 46. Resistor $R_5$ of high pass filter circuit 90 has a first terminal connected to a terminal of capacitor $C_5$ and the first terminal of telemetry module 46 and a second terminal connected to a reference, such as ground.

Unlike high pass filter circuit 80 of FIG. 6, high pass filter circuit 90 does include components coupled between the second terminal of $L_{ant}$ and the second terminal of inductive telemetry module 46. In the example of FIG. 7, a first terminal of resistor $R_6$ of high pass filter circuit 90 is connected between the second terminal of $L_{ant}$ and the second terminal of telemetry module 46 and a second terminal of resistor $R_6$ is connected to a reference, such as ground. As such, high pass filter circuit 90 operates as a quasi-differential high pass filter circuit.

The resistive and capacitive values of $R_5$ and $R_6$ and capacitor $C_5$, respectively, are selected such that high pass filter circuit 90 operates to substantially block signals induced on the inductive antenna by varying magnetic fields generated from a source of interference and substantially pass signals induced on the inductive antenna by varying magnetic fields generated by an expected source. In this particular example, high pass filter circuit 90 substantially blocks signals from gradient magnetic fields 11 of MRI scanner 16, which occur at frequencies less than 10 kHz, and pass telemetry signals from programming device 18, which occur around approximately 175 kHz. As such, the components of filter circuit 90 are selected to substantially block the signals of the interfering varying magnetic fields. In one example, $R_5$ and $R_6$ have values approximately equal to 10 kΩ and capacitor $C_5$ has a value of approximately 18 nF. However, other capacitive and/or resistive values may be used to form high pass filter circuit 90. Moreover more or fewer capacitors and resistors may be used.

In the example high pass filters above, the cutoff frequency (Fc) is equal to $$Fc = \frac{1}{2 * \pi * R * C}$$

and the values of R and C may be selected to cutoff the frequency of interest, e.g., 10 kHz in the examples described above.

Figure 8:
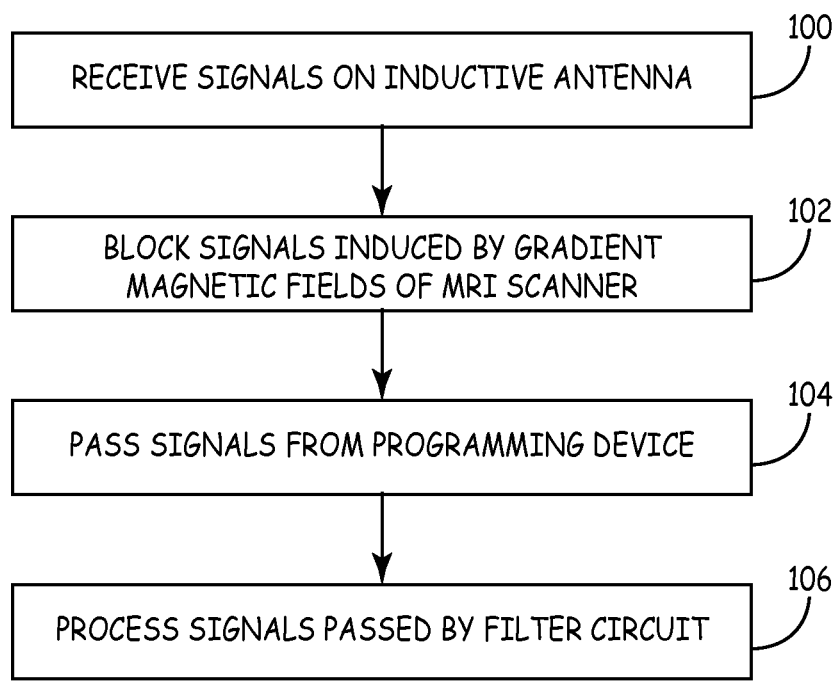
FIG. 8 is a flow diagram illustrating example operation of an IMD operating in accordance with the techniques of this disclosure.

FIG. 8 is a flow diagram illustrating example operation of an IMD operating in accordance with the techniques of this disclosure. Initially, an inductive antenna 42 of the IMD receives a signal via inductive coupling (100). Some of the signals induced on inductive antenna 42 are expected and desirable, such as telemetry signals inductively coupled via telemetry head 20 connected to programming device 18 (FIG. 1). However, other signals induced on inductive antenna 42 are undesirable, such as signals induced on inductive antenna 42 by varying magnetic fields of a source of interference (e.g., gradient magnetic fields 11 of MRI scanner 16 of FIG. 1).

To reduce the adverse effects of the undesirable signals induced by gradient magnetic fields 11 of MRI scanner 16, filter circuit 44 of the IMD substantially blocks signals from sources of interference, such as those induced by gradient magnetic fields 11 of MRI scanner 16 (102). Filter circuit 44 of the IMD substantially passes signals from desirable sources, such as telemetry from programming device 18 (104). Filter circuit 44 may, in one example, include one or more capacitors and resistors arranged to form a high pass filter that substantially passes desired telemetry signals while substantially blocking undesired signals induced by gradient magnetic fields 11 generated by MRI scanner 16. Example high pass filters are illustrated in FIGS. 5-7. In other examples, filter circuit 44 may include one or more capacitors, resistors and/or inductors arranged to form a band pass filter that substantially passes only the frequency associated with the desired telemetry signals or a band stop filter that substantially blocks the frequency associated with gradient magnetic fields 11 of MRI scanner 16.

Inductive telemetry module 46 processes the signals passed by filter circuit 44 (106). In this manner, filter circuit 44 reduces, and possibly eliminates, adverse effects caused by undesirable signals, such as damage to one or more components of the IMD and/or undesirable heating of the IMD, while allowing the IMD to use inductive telemetry.

The techniques described in this disclosure may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. An implantable medical device comprising:
   an inductive antenna that receives signals via inductive coupling, wherein the inductive antenna is located within a conductive, non-magnetic housing of the implantable medical device;
   a filter circuit that attenuates signals induced on the inductive antenna by varying magnetic fields generated from a source of interference and substantially passes signals induced on the inductive antenna by varying magnetic fields generated by an expected source; and
   a telemetry module that processes the signals from the filter circuit.

2. The device of claim 1, wherein the antenna comprises a loop antenna that includes one or more conductive loops.

3. The device of claim 2, wherein the loop antenna has a loop area that is greater than or equal to approximately one square inch.

4. The device of claim 1, wherein the current induced on the inductive antenna by the varying magnetic fields generated from the source of interference is greater than or equal to approximately twenty-five milliamps.

5. The device of claim 1, wherein the filter comprises one of a high-pass filter, a band-pass filter and a band-stop filter.

6. The device of claim 1, wherein the filter attenuates signals that are less than approximately 10 kilohertz.

7. The device of claim 6, wherein the filter passes signals at approximately 175 kilohertz.

8. The device of claim 1, wherein the device housing shields the antenna from radio frequency (RF) signals.

9. The device of claim 1, wherein the inductive antenna comprises a first antenna and the device further comprises a second antenna that receives signals via radio frequency (RF) coupling.

10. The device of claim 1, wherein the source of interference comprises a magnetic resonance imaging (MRI) device.

11. The device of claim 1, wherein the telemetry module and the filter circuit are separate components.

12. An implantable medical device comprising:
means for receiving signals via inductive coupling;
means for filtering the received signals to attenuate signals induced on the inductive antenna by varying magnetic fields generated from a source of interference and substantially pass signals induced on the inductive antenna by varying magnetic fields generated by an expected source;
means for processing the signals from the filter circuit, wherein the means for processing the signals and the means for filtering the received signals are separate components; and
means for shielding the inductive antenna from radio frequency (RF) signals.

13. The device of claim 12, wherein the means for receiving the signals comprises an inductive antenna.

14. The device of claim 13, wherein the inductive antenna comprise a loop antenna that includes one or more conductive loops.

15. The device of claim 14, wherein the loop antenna has a loop area that is greater than or equal to approximately one square inch.

16. The device of claim 14, wherein the current induced on the inductive antenna by the varying magnetic fields generated from the source of interference is greater than or equal to approximately twenty-five milliamps.

17. The device of claim 12, wherein means for filtering comprises one of a high-pass filter, a band-pass filter and a band-stop filter.

18. The device of claim 12, wherein the means for filtering attenuates signals that are less than approximately 10 kilohertz.

19. The device of claim 18, wherein the means for filtering passes signals at approximately 175 kilohertz.

20. The device of claim 12, wherein the means for shielding the inductive antenna comprises a conductive, non-magnetic housing of the implantable medical device.

21. The device of claim 12, further comprising means for receiving signals via radio frequency (RF) coupling.

22. The device of claim 12, wherein the source of interference comprises a magnetic resonance imaging (MRI) device.

* * * * *